United States Patent [19]
Tatar

[11] Patent Number: 6,113,601
[45] Date of Patent: Sep. 5, 2000

[54] POLYAXIAL PEDICLE SCREW HAVING A LOOSELY COUPLED LOCKING CAP

[75] Inventor: Stephen Tatar, Montvale, N.J.

[73] Assignee: Bones Consulting, LLC, Summit, N.J.

[21] Appl. No.: 09/096,815

[22] Filed: Jun. 12, 1998

[51] Int. Cl.[7] .................................................. A61B 17/56
[52] U.S. Cl. ............................................................. 606/61
[58] Field of Search .............................. 606/61, 62, 63, 606/60

[56] References Cited

U.S. PATENT DOCUMENTS

| | | | |
|---|---|---|---|
| 5,882,350 | 3/1999 | Ralph et al. | 606/61 |
| 5,885,286 | 3/1999 | Sherman et al. | 606/61 |
| 5,891,145 | 4/1999 | Morrison et al. | 606/61 |

*Primary Examiner*—Michael Buiz
*Assistant Examiner*—(Jackie) Tan-Uyen T. Ho
*Attorney, Agent, or Firm*—Joseph P. Errico, Esq.

[57] ABSTRACT

A polyaxial pedicle screw for use with rod implant apparatus includes a rod receiving body, a screw having a curvate head, a compression element, and a means for loosely and reversibly maintaining a coupled relationship between the compression element and the screw head during angulation thereof relative to the rod receiving body, while still permitting compressive locking of the assembly in a specific orientation by means of a compressive force applied by a rod onto the compression element and the head of the screw.

8 Claims, 2 Drawing Sheets

POLYAXIAL PEDICLE SCREW HAVING A LOOSELY COUPLED LOCKING CAP

BACKGROUND OF THE INVENTION

1. Field of the Invention

This invention relates generally to a polyaxial screw and coupling apparatus for use with orthopedic fixation systems. More particularly, the present invention relates to a screw for insertion into spinal bone, and a coupling element polyaxially mounted thereto for coupling the screw to an orthopedic implantation structure, such as a rod, therein enhancing the efficacy of the implant assembly by providing freedom of angulation among the rod, screw and coupling element.

2. Description of the Prior Art

The spinal column is highly complex system of bones and connective tissues which houses and protects critical elements of the nervous system and the arterial and veinous bodies in close proximity thereto. In spite of these complexities, the spine is a highly flexible structure, capable of a high degree of curvature and twist through a wide range of motion.

Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve this immobilization by implanting artificial assemblies in or on the spinal column. These assemblies may be classified as anterior, posterior, or lateral implants. As the classification suggests, lateral and anterior assemblies are coupled to the anterior portion of the spine, which is the sequence of vertebral bodies. Posterior implants are attached to the back of the spinal column, generally hooking under the lamina and entering into the central canal, attaching to the transverse process, or coupling through the pedicle bone. The present invention relates to spinal fixation devices for immobilizing and altering the alignment of the spine over a large number, for example more than three or four, vertebra by means of affixing at least one elongate rod to the sequence of selected bones.

Such "rod assemblies" generally comprise a plurality of screws which are implanted through the posterior lateral surfaces of the laminae, through the pedicles, and into their respective vertebral bodies. The screws are provided with coupling elements, for receiving an elongate rod therethrough. The rod extends along the axis of the spine, coupling to the plurality of screws via their coupling elements. The aligning influence of the rod forces the spine to which it is affixed, to conform to a more proper shape.

It has been identified, however, that a considerable difficulty is associated with inserting screws along a misaligned curvature and simultaneously exactly positioning the coupling elements such that the receiving loci thereof are aligned so that the rod can be passed therethrough without distorting the screws. Attempts at achieving proper alignment with fixed screws is understood to require considerably longer operating time, which is known to increase the incidence of complications associated with surgery. Often such alignments, with such fixed axes devices could not be achieved, and the entire instrumentationing effort would end unsuccessfully.

In addition, for many patients specific pathology it is desirable that the rod extend down into and beyond the lumbar portion of the spine, and for the end of the rod to be coupled to the sacral bone. Providing such an end to the assembly in the sacral bone has been understandably suggested inasmuch as it provides superior support to the fall extent of the assembly. The most suitable position for the insertion of the screws into the sacral body may not, however, conform to the direction extent of the rod as it is affixed to the entirety of the assembly. Misalignment of the rod with respect to the screw and the coupling element is often a source of considerable disadvantage for the surgeon, often requiring considerable efforts to be expended bending and aligning the rod with the receiving locus of the coupling element. These additional efforts are a considerable difficulty associated with the proper and expeditious affixation, and over the long term, the offset of the rod can have a deleterious effect on the overall performance of the entire implantation assembly.

The art contains a variety of attempts at providing instrumentation which permit a freedom with respect to angulation of the screw and the coupling element. These teachings, however, have generally been complex, and inadequately reliable with respect to durability. The considerable drawbacks associated with the prior art systems include complexity, difficulty properly positioned the rod and coupling elements, and the tedious manipulation of the many parts associated with the complex devices.

It is, therefore, the principal object of the present invention to provide a pedicle screw and coupling element assembly which provides a polyaxial freedom of implantation angulation with respect to rod reception.

In addition, it is an object of the present invention to provide such an assembly which comprises a reduced number of elements, and which correspondingly provides for expeditious implantation.

Accordingly it is also an object of the present invention to provide an assembly which is reliable, durable, and provides long term fixation support.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a polyaxial locking pedicle screw device for use with rod stabilization and immobilization systems in the spine. Stated concisely, the present invention is a polyaxial pedicle screw for use with rod implantation apparatus, comprising:

a bone screw having a shaft and a curvate head, said curvate head including an annular recess formed therein;

a body element including an axial interior passage extending through the element from a proximal upper end to a distal lower end, said distal lower end having an inwardly tapered surface defining a socket wherein said curvate head may be polyaxially mounted such that said shaft may extend out from said lower end of said body and polyaxially rotate through a range of angles relative to said body element, said range of angles including non-anally parallel ones, said proximal upper end including a rod receiving channel and a pair of upwardly extending members having a threading disposed thereon;

a compression element having a curvate upper exterior surface and a concave interior surface, said concave interior surface being curvate and being rotationally seatable on the curvate head of said bone screw, said concave interior surface further including an annular recess;

means for loosely coupling said compression element to said curvate head of said bone screw, said means being positionable within said annular recesses of said curvate head and said compression element; and a locking nut, mateable with the threading on the upwardly extending members of the body element, for compressing a rod into the channel of the body, and onto the compression element, thereby imparting a compression force onto the head of the screw which rigidly locked the head against the inwardly tapered surface at the distal lower end of the body element.

Stated alternatively, the present invention is a bone screw for connecting a bone with a rod, said bone screw comprising:

a screw member having a threaded portion and a head, said head having a spherical segment-shaped portion and a recess formed therein;

a receiver member for receiving said head of said screw member and said rod, said receiver member having a first end and a second end, a bore provided in said receiver member between said first and second ends, a hollow spherical portion in said bore for receiving said head at a position inwards of said second end, said receiver member further having a substantially U-shaped cross-section with two free legs which are provided with a thread;

a pressure means having a portion acting on said head, said portion acting on said head including a recess formed therein;

coupling means for loosely coupling said pressure means to said head of said screw member, said coupling means engaging said pressure means and said head at each of said recesses, and a locking nut screwed onto said thread of said receiver member.

More particularly, the polyaxial screw assembly of the present invention comprises: a cylindrical body portion having a medial channel for receiving a rod; a bone screw having a head which is curvate in shape which is maintained within a bottom end of the cylindrical body; a concentric floating compression element mounted onto the curvate head of the screw; a coupling means, which seats in an annular recess of the screw head, and loosely maintains a mutual engagement of the compression element to the screw head; and a locking nut for engaging the upper portion of the body, which provides compression of the rod onto the coupling element, which in turn locks the head of the screw in the bottom of the body.

As introduced above, the body portion may be conceptually divided into three sections. First, there is a lower socket portion for retaining the compression element, the coupling means, and the head of the screw. This lower socket portion further includes an inwardly directed annular lip which supports the head of the screw while permitting the shaft of the screw to extend downwardly and through an axial opening in the base thereof. The opening and the lip are of sufficient dimensions relative to the head and shaft of the screw, that the shaft may extend outwardly from the body at a range of angles relative to the body, said angle including angles which are parallel to the long axis of the body, as well as angles which are not parallel to said axis. The lip further defines an inwardly directed ledge which provides a rotational stop for the floating compression element (see below).

The rod receiving medial portion of the body comprises a channel wherein the rod of the implant apparatus is mounted. More particularly, the walls of the hollow cylindrical body include opposing vertically oriented channels, having curvate bottom surfaces thereof, and which extend downward from the top of the element to a position above the lower portion. The channels divide the walls of the intermediate and upper portions of the cylindrical body into two upwardly extending members, between which the rod receiving channel is disposed.

The upper portion of the upwardly extending members of the element comprise an external surface threading onto which a locking nut may be disposed to provide a downward force.

The screw comprises a threaded shaft which has a dimension which permits it to extend through the opening in the bottom of the body portion. The head of the screw, however, is a curvate, e.g. ball-shaped, and has a maximum diameter which is larger than the diameter of the opening formed by the lip of the lower body portion. This relative sizing permits the screw head to be retained in the lower portion of the body, while the shaft extends through and polyaxially rotates through the bottom of the body.

In addition, the head of the screw includes a recess suited for receiving a screwdriving tool, so that the screw may be manually driven into the pedicle bone. The head of the screw further includes an annular recess, the plane defined by said recess being substantially perpendicular to the axis of the screw.

The floating compression element comprises a semi-spherical inverted bowl shape, designed to seat onto the top of the screw head and to slide over the head. The center of the compression element further includes an opening, through which said screwdriving tool may be inserted so as to engage the head of the screw. In a first embodiment of the compression element, the inner curvate surface of the compression element includes an annular recess into which a snap ring maybe fitted. This snap ring expands to fully seat into the recess of the compression element when a outwardly directed radial force is applied to the ring. In its unexpanded rest state, the snap ring seat partially in the annular recess of the compression element, and partially into the inner volume of the element.

The first step in the process of assembling this first embodiment comprises placing the head of the screw into the concave recess of the compression element such that the snap ring is first expanded into the recess of the compression element, and then permitted to contract partially into the annular recess of the head of the screw. In this configuration the screw head and the compression element are loosely held together by the mutual engagement of the snap ring, such that the opening in the compression element is aligned with the opening in the head of the screw. The combination of the screw, snap ring, and compression element are then advanced downwardly through the top of the body until the head of the screw rests against the lip of the lower portion of the axial bore.

In a second embodiment, the compression element does not comprise an annular recess, nor is there a snap ring used to loosely hold the compression element on the head of the screw. In this embodiment, the compression element includes a complement of flexible pins disposed through the cup wall, and exposing themselves as minor arcs on the inside surface of the element. These pins engage the annular recess of the screw head in much the same manner as the snap ring of the first embodiment, thereby loosely holding the screw head and the compression element in relative position.

In each of these embodiments, the loose engagement of the compression element on the screw head is reversible insofar as the mutual rotation of the screw and element can occur through a range of angles relative to the body, up to the point where the lower edge of the compression element contacts the ledge formed by the lip of the lower portion of the body. Continued angulation of the screw will require a disengagement of the mutual coupling of the compression element and the screw head. In the first embodiment, sufficient rotational force (applied by the surgeon to the pre-tightened assembly) causes the snap ring to expand and for the engagement of the snap ring in the annular recess of the screw head to cease, thus permitting the screw to rotate relative to the compression element. Similarly, the flexible pins of the second embodiment flex under sufficient load, thus freeing the screw head from the retention of the pins in its annular recess.

The insertion of a rod into the channel of the medial portion of the body, brings the rod down onto the compression element. Securing the rod in the channel by means of a top locking nut drives the rod into the channel, and onto the compression element, which in turn compresses against the head of the screw. As the head of the screw is prevented from downward translation by the lip of the body, the force applied from above simply compression locks the entire assembly in whatever angular configuration it is placed.

It shall be understood that additional features, such as means for preventing the screw head and the compression element from backing up through the body prior to insertion of the rod into the channel (e.g. a retaining snap ring disposed in the body wall), are obvious modifications of the present invention, and are hereby fully anticipated.

Multiple individual pedicle screw assemblies are generally necessary to complete the full array of anchoring sites for the rod immobilization system, however, the pedicle screw of the present invention is designed to be compatible with alternative rod systems so that, where necessary, the present invention may be employed to rectify the failures of other systems the implantation of which may have already begun.

BRIEF DESCRIPTION OF THE FIGURES

FIG. 4 is a side cross section view of a snap ring which is used with the first embodiment of the present invention utilizing the compression element as shown in FIG. 3a;

DETAILED DESCRIPTION OF THE PREFERRED EMBODIMENT

While the present invention will be described more fully hereinafter with reference to the accompanying drawings, in which particular embodiments are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 1:
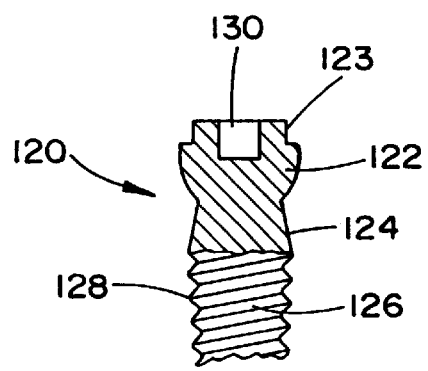
FIG. 1 is a side view of a screw having a curvate head and annular recess which are aspects of the present invention.

Referring now to FIG. 1, a side view of the screw portion of the present invention, comprising a curvate head and an annular recess, is shown. The screw 120 comprises a head portion 122, a neck 124, and a shaft 126. In FIG. 1, the shaft 126 (partially shown) is illustrated as having a high pitch thread 128. It shall be understood that a variety of shaft designs are interchangeable with the present invention. The specific choice of shaft features, such as thread pitch, shaft diameter to thread diameter ratio, and overall shaft shape, should be made be the physician with respect to the conditions of the individual patient's bone, however, this invention is compatible with a wide variety of shaft designs.

The head portion 122 of the screw 120 comprises a curvate shape, which has an axial recess 130 formed therein for a screwdriving tool to engage and apply a downward rotational force thereonto it. In addition, the head 122 further includes an annular recess 123. This annular recess is provided for engaging the loose coupling means described more fully hereinbelow with respect to FIGS. 3a–7. It shall be understood that the curvate shape of the head 122 is preferably a semi-spherical shape, which is a section of a sphere. In the embodiment shown, the section is greater in extent than a hemisphere, and it correspondingly exhibits an external contour which is equidistant from a center point of the head.

The recess 130 defines a receiving locus for the application of a torque for driving the screw 120 into the bone. The specific shape of the recess 122 may be chosen to cooperate with any suitable screw-driving tool. For example, the recess 130 may comprise a slot for a flat-headed screwdriver, a crossed recess for a phillips head screwdriver, or most preferably, a hexagonally shaped hole for receiving an allen wrench. It is further preferable that the recess 130 be co-axial with the general elongate axis of the screw 120, and most particularly with respect to the shaft 126. Having the axes of the recess 130 and the shaft 126 co-linear facilitates step of inserting the screw 120 into the bone.

Figure 6:
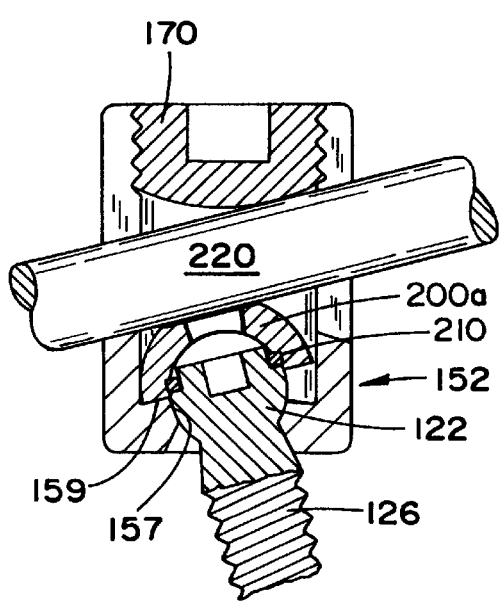
FIG. 6 is a side cross section view of the present invention utilizing the compression element of FIG. 3a in its fully assembled disposition having a rod securely locked therein.
Figure 7:
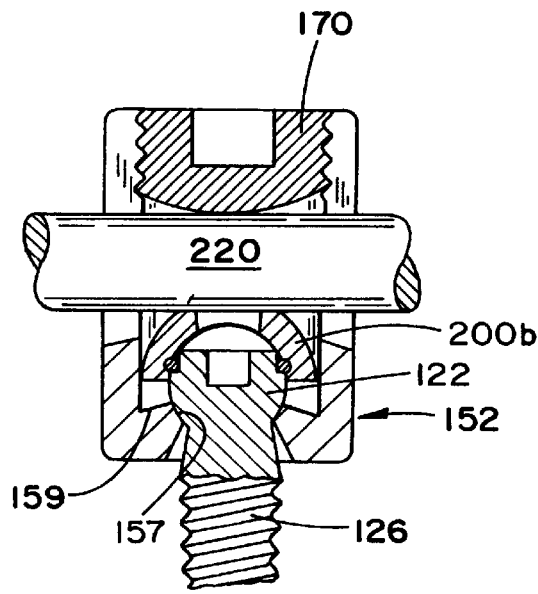
FIG. 7 is a side cross section view of the present invention utilizing the compression element of FIG. 3b in its fully assembled disposition having a rod securely locked therein.

The curvate head portion 122 is connected to the shaft 126 at a neck portion 124. While it is preferable that the diameter of the shaft 126 be less than the diameter of the semi-spherical head 122, it is also preferable that the neck 124 of the screw 120 be narrower than the widest portion of the shaft 126. This preferable dimension permits the screw to be locked at a variety of angles while still being securely joined to the coupling element (embodiments of which are shown in FIGS. 6 and 7).

Figure 2:
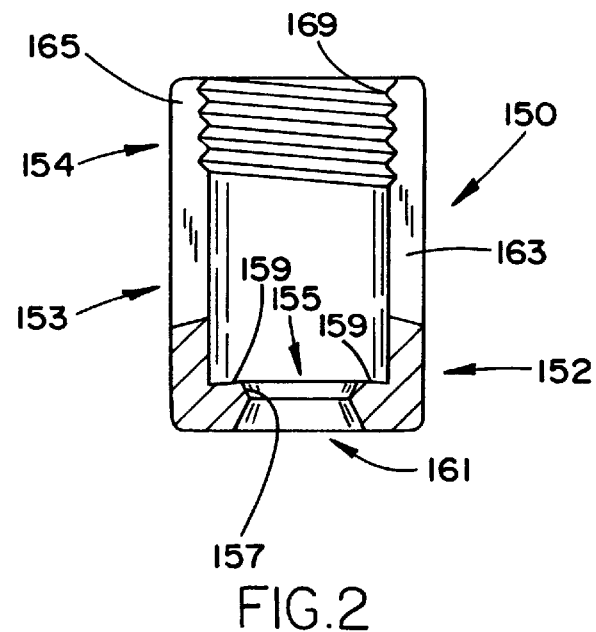
FIG. 2 is a side cross section view of the body of present invention, wherein critical interior features of the element are shown.

Referring now to FIG. 2, a first embodiment of the body portion 150 of the present invention is shown in a side cross-section view. The coupling element 150 comprises a generally cylindrical tubular body, having an axial bore 151, and which may be conceptually separated into a lower portion 152, a middle portion 153, and an upper portion 154, each of which shall be described more fully hereinbelow. First, the lower portion 152 comprises a socket 155 for retaining the compression element (see FIGS. 3a and 3b and the head 122 of the screw 120. This lower socket portion further includes an inwardly directed annular lip 157 which supports the head 122 of the screw, when positioned therein, while permitting the shaft of the screw to extend downwardly and through an axial opening 161 in the base thereof. The opening and the lip are of sufficient dimensions relative to the head and shaft of the screw, that the shaft may extend outwardly from the body at a range of angles relative to the body, said angle including angles which are parallel to the long axis of the body, as well as angles which are not parallel to said axis. The lip further defines an inwardly directed ledge 159 which provides a rotational stop for the floating compression element (see below).

The rod receiving medial portion 153 of the body comprises a channel 163 wherein the rod of the implant apparatus is mounted. More particularly, the walls of the hollow cylindrical body include opposing vertically oriented channels, formed between upwardly extending members 165.

The upper portion 154 of the body 150, which comprises only the upwardly extending members 165, further comprises an interior surface threading 169 onto which a locking nut (see FIG. 5) may be disposed to provide a downward force onto a rod disposed in the channel 163.

Figure 5:
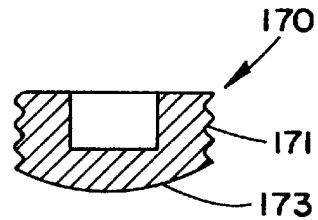
FIG. 5 is a cross section view of a top locking nut for use with the present invention.

More particularly, referring now to FIG. 5, a top locking set screw-styled nut 170 is shown in a side cross-section view. The nut 170 comprises an external threading 171 which is intended to mate with the threading 169 on the upwardly extending members 165 of the upper portion 154 of the body portion 150. The bottom surface 173 of the nut is rounded so that it may seat against the rod, independent of the rods relative orientation to the body 150.

Figure 3A:
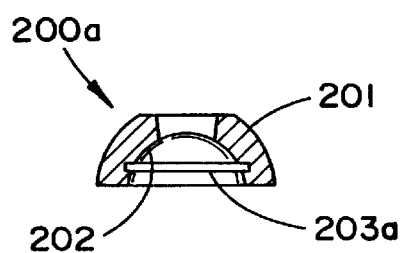
FIGS. 3a and 3b are side cross section views of first and second embodiments of a compression element of the present invention, respectively.
Figure 3B:
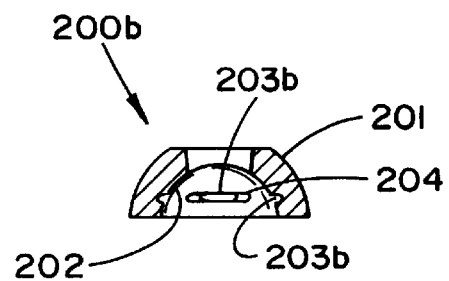

Referring now to FIGS. 3a and 3b, the loosely mounting compression elements 200a and 200b are shown in a side cross-section views. Each of the elements 200a,200b comprises a convex exterior surface 201 and a concave interior surface 202, thus forming an inverted bowl-shape. The interior surface 202 of each is designed to mate and float on the curvate head 122 of the screw 120. In the embodiment of FIG. 3a, the interior surface 202 further includes an annular recess 203a. The embodiment of FIG. 3b, alternatively, includes at least one pair of through holes 204 which extend through the exterior of the compression element 200b, and which tangentially cut through the interior surface 202 of the element. These through holes thereby form recesses 203b in the inner surface 202, through which holes and recesses at least one corresponding flexible pin (not shown) may be inserted.

Figure 4:

Referring now to FIG. 4, a snap ring 210 is shown in a side cross section view. The snap ring 210 is a simple device comprised of a circular ring of material having a single radial (or substantially radial) cut 211 which renders the ring radially expandable and contractable if acted upon by the appropriate radial force. This snap ring 210 has a resting outer diameter which is greater than the inner diameter of the annular recess 203a formed in the interior surface 202 of the loose compression element 200a. The inner resting diameter of the ring is, however, smaller than the inner diameter of the annular recess 203a formed in the interior surface 202 of the loose compression element 200a, and simultaneously smaller than the outer diameter of the annular recess 123 formed in the head 122 of the screw 120. When placed in the compression element, and then mounted to the screw, the snap-ring contracts and expands accordingly, such that the screw and the element are rendered loosely coupled (each remains free to rotate relative to the other about the elongate axis of the screw, but can neither easily separate axially nor rotate independently out of the axial direction).

Once this coupling of the screw to the compression element has been introduced, and the screw shaft inserted through the axial bore 151 of the body 150, until the head 122 engages the lip 157 of the lower socket portion 152, the head 122 of the screw is loosely incarcerated within the socket. This loose incarceration does not prevent the screw and shaft from polyaxially rotating within, and relative to, the body. During this motion, however, the compression element rotates with the screw (until the lower rim of the element 200a contacts the ledge 159 of the socket 152).

Similarly, the compression element 200b, utilizes flexible pins extending through the inner surface 202 of the element, to achieve an equivalent loose coupling of the compression element to the screw head 122.

Referring now to FIGS. 6 and 7, which show side cross-section views of the fully locked assemblies of the present embodiments (and more particularly, the embodiments utilizing a snap ring and flexible pins, respectively, to loosely couple the compression element to the screw), the assembly and functional use of the present invention is now described. The loosely combined screw 120 and compression element 200a,200b are positioned such that the head 122 of the screw 120 is seated against the lip 157 of the socket 152. The screw shaft 126 is polyaxially rotated into the relative position (relative to the body 150) which is best suited for fixation to the patient's bone. The body portion 150, is independently rotated into the ideal position for receiving the rod 220 of the implant apparatus. If the body portion 150 and the screw 120 require greater rotation than is permitted by the loose coupling of the compression element 200a,200b and the screw head 122 (because the edge of the compression element has already rotated into contact with the ledge 159 of the socket) the loose coupling releases and the screw can continue to turn relative to the body 150. It is important to realize that this feature does not diminish the locking strength of the assembly, as it does not diminish the contact force which can be provided to the head 122 of the screw by and between the compression element 200a,200b and the socket lip 157 once the rod 220 and nut 170 begin to compress downwardly. More particularly, once the rod has been inserted into the channel 163 of the body 150, and the nut 170 is advanced onto the threading 169 of the body, a compressive force builds up on the compression element 200a,200b, thus applying a crush locking force onto the head 122 of the screw, independent of its position relative to the body.

While there has been described and illustrated embodiments of a polyaxial screw assembly for use with posterior spinal rod implantation apparatus, it will be apparent to those skilled in the art that variations and modifications are possible without deviating from the broad spirit and principle of the present invention. The present invention shall, therefore, be limited solely by the scope of the claims appended hereto.

I claim:

1. A polyaxial pedicle screw for use with rod implantation apparatus, comprising:

a bone screw having a shaft and a curvate head, said curvate head including an annular recess formed therein;

a body element including an axial interior passage extending through the element from a proximal upper end to a distal lower end, said distal lower end having an inwardly tapered surface defining a socket wherein said curvate head may be polyaxially mounted such that said shaft may extend out from said lower end of said body and polyaxially rotate through a range of angles relative to said body element, said range of angles including non-axially parallel ones, said proximal upper end including a rod receiving channel and a pair of upwardly extending members having a threading disposed thereon;

a compression element having a curvate upper exterior surface and a concave interior surface, said concave interior surface being curvate and being rotationally seatable on the curvate head of said bone screw, said concave interior surface further including an annular recess;

means for loosely coupling said compression element to said curvate head of said bone screw, said means being positionable within said annular recesses of said curvate head and said compression element, wherein said means includes a snap ring; and a locking nut, mateable with the threading on the upwardly extending members of the body element, for compressing a rod into the channel of the body, and onto the compression element, thereby imparting a compression force onto the head of the screw which rigidly locked the head against the inwardly tapered surface at the distal lower end of the body element.

2. The assembly as set forth in claim 1, wherein said curvate head is semi-spherical.

3. The assembly as set forth in claim 1, wherein said compression element further includes a plurality of holes extending from the exterior surface to the annular recess, and wherein said means for loosely coupling said compression element to said curvate head of said bone screw comprises a corresponding plurality of flexible pins which seat in said holes and engage the annular recess of said curvate head of said screw.

4. A orthopedic rod implantation apparatus having polyaxial screw and coupling elements, comprising:

at least one elongate rod;

at least one polyaxial screw including;

a bone screw having a shaft and a curvate head, said curvate head including an annular recess formed therein;

a body element including an axial interior passage extending through the element from a proximal upper end to distal lower end, said distal lower end having an inwardly tapered surface defining a socket wherein said curvate head may be polyaxially mounted such that said shaft may extend out from said lower end of said body and polyaxially rotate through a range of angles relative to said body element, said range of angles including non-axially parallel ones, said proximal upper end including a rod receiving channel and a pair of upwardly extending members having a threading disposed thereon;

a compression element having a curvate upper exterior surface and a concave interior surface, said concave interior surface being curvate and being rotationally seatable on the curvate head of said bone screw, said concave interior surface further including an annular recess;

means for loosely coupling said compression element to said curvate head of said bone screw, said means being positionable within said annular recesses of said curvate head and said compression element, wherein said means for loosely coupling said compression element to said curvate head of said bone screw comprises a snap ring; and a locking nut, mateable with the threading on the upwardly extending members of the body element, for compressing said rod into the channel of the body, and onto the compression element, thereby imparting a compression force onto the head of the screw which rigidly locked the head against the inwardly tapered surface at the distal lower end of the body element.

5. The assembly as set forth in claim 4, wherein said curvate head is semi-spherical.

6. The assembly as set forth in claim 4, wherein said compression element further includes a plurality of holes extending from the exterior surface to the annular recess, and wherein said means for loosely coupling said compression element to said curvate head of said bone screw comprises a corresponding plurality of flexible pins which seat in said holes and engage the annular recess of said curvate head of said screw.

7. A bone screw for connecting a bone with a rod, said bone screw comprising:

a screw member having a threaded portion and a head, said head having a spherical segment-shaped portion and a recess formed therein;

a receiver member for receiving said head of said screw member and said rod, said receiver member having a first end and a second end, a bore provided in said receiver member between said first and second ends, a hollow spherical portion in said bore for receiving said head at a position inwards of said second end, said receiver member further having a substantially U-shaped cross-section with tow free legs which are provided with a thread;

a pressure means having a portion acting on said head, said portion acting on said head including a recess formed therein;

coupling means for loosely coupling said pressure means to said head of said screw member, said coupling means engaging said pressure means and said head at each of said recesses, wherein said means for loosely coupling said compression element to said curvate head of said bone screw comprises a snap ring; and a locking nut screwed onto said thread of said receiver member.

8. The assembly as set forth in claim 7, wherein said compression element further includes a plurality of holes extending from the exterior surface to the annular recess, and wherein said means for loosely coupling said compression element to said curvate head of said bone screw comprises a corresponding plurality of flexible pins which seat in said holes and engage the annular recess of said curvate head of said screw.

* * * * *